United States Patent [19]

Philip, Jr. et al.

[11] Patent Number: 4,914,015
[45] Date of Patent: Apr. 3, 1990

[54] RED AND INFRARED FILMS CONTAINING 5-SUBSTITUTED-THIO-1,2,3,4-THIATRIAZOLES AND 5-SUBSTITUTED-OXY-1,2,3,4-THIATRIAZOLES

[75] Inventors: James B. Philip, Jr., Mahtomedi; Craig A. Perman, Woodbury; Peter D. Sills, St. Paul, all of Minn.

[73] Assignee: Minnesota Mining and Manufacturing Company, St. Paul, Minn.

[21] Appl. No.: 258,497

[22] Filed: Oct. 17, 1988

[51] Int. Cl.$^4$ ................................................ G03C 1/28
[52] U.S. Cl. ..................................... 430/572; 430/576; 430/600; 430/611; 430/614
[58] Field of Search ............... 430/572, 576, 600, 614, 430/611

[56] References Cited

U.S. PATENT DOCUMENTS 4,596,767  6/1986  Mihara et al. ...................... 430/576
4,780,404 10/1988  Sills et al. ......................... 430/576

FOREIGN PATENT DOCUMENTS 2270909 11/1987 Japan ................................ 430/614

Primary Examiner—Paul R. Michl
Assistant Examiner—Thorl Chea
Attorney, Agent, or Firm—Donald M. Sell; Walter N. Kirn; Mark A. Litman

[57] ABSTRACT 5-substituted-thio-1,2,3,4-thiatriazoles and 5-substituted-oxy1,2,3,4-thiatriazoles have been found to be supersensitive for silver halide photographic emulsions spectrally sensitized to the red and infrared regions of the electromagnetic spectrum.

28 Claims, No Drawings

RED AND INFRARED FILMS CONTAINING 5-SUBSTITUTED-THIO-1,2,3,4-THIATRIAZOLES AND 5-SUBSTITUTED-OXY-1,2,3,4-THIATRIAZOLES

FIELD OF INVENTION

This invention relates to photographic elements, particularly to infrared and red sensitive elements, and more particularly to compounds useful in (1) supersensitizing and (2) improving the keeping properties of the coated infrared and red sensitive materials.

BACKGROUND OF THE INVENTION

In most uses of silver halide in photographic materials, it is desirable to increase the speed or sensitivity of the emulsion. There are a number of different techniques for increasing the speed of an emulsion which are usually classified as chemical sensitization or spectral sensitization. Chemical sensitization usually involves modification of the silver halide grains to make the most efficient use of the radiation that they absorb. The three general types of chemical sensitization are sulfur sensitization, reduction sensitization, and precious (noble) metal sensitization. These methods of chemical sensitization are well known and firmly established in the art (e.g., James, T. H. and Vanselow, W. "Chemical Sensitization", J. Photo. Sci., 1, 133 (1953), Freiser, H. and Ranz, E., Ber. der Bunsengesellschaft, 68, 389 (1964), and Pouradier, J. "Chemical Sensitization", Photographic Theory: Liege Summer School, A. Hautot, p. 111, Focal Press (London 1963).

Spectral sensitization enables grains to benefit from radiation in regions of the electromagnetic spectrum where the silver halide would ordinarily not absorb. Dyes which absorb radiation and can transfer energy to the grains to help in the photoreduction of silver ions to clusters of silver metal are conventionally used to effect spectral sensitization.

Another phenomenon associated with the use of spectral sensitizing dyes is known in the art as supersensitization. The addition of other substances, frequently in quantities ranging from less than an equivalent molar rate to a 100 fold molar excess of supersensitizer to dye, can increase the spectrally sensitized speed of the emulsion by more than an order of magnitude. Some supersensitizers are dyes themselves, but many others do not absorb radiation in significant amounts in the visible portion of the electromagnetic spectrum. Therefore, the effect of supersensitizers on spectral sensitization is not clearly dependent on the ability of compounds to absorb radiation in the visible portion of the spectrum. Certain cyanines, merocyanines compounds analogous to cyanines, certain acylmethylene derivatives of heterocyclic bases, and ketone derivatives such as p-dimethylaminobenzalacetone are known supersensitizers. An expanded selection of supersensitizers is therefore desired.

Silver halide emulsions can be protected against the production of fog and stabilized against the loss of sensitivity during keeping. Suitable antifoggants and stabilizers which can be used alone or in combination, include triphenylphosphines, amines, arsines, bismuthines, and stibildynes taught in U.S. Pat. No. 4,578,347; the thiazolium salts described in Staud, U.S. Pat. No. 2,131,038 and Allen, U.S. Pat. No. 3,694,716; the azaindenes described in Piper, U.S. Pat. No. 2,886,437 and Heimbach, U.S. Pat. No. 2,444,605; the mercaptotetrazoles described in Kendall et al., U.S. Pat. No. 2,403,977, Kennard et al., U.S. Pat. No. 3,266,897 and Luckey et al., U.S. Pat. No. 3,397,987; and the oximes described in Carroll et al., British Pat. No. 623,448. With respect to infrared sensitive emulsions, G.B. Pat. No. 2,140,928 describes the use of heterocyclic indolinium dyes to maintain stability.

However, it is well known in the prior art that infrared sensitive photographic materials exhibit poor keeping properties (Neblette's Handbook of Photography and Reprography, 7th. Edition, Ed. Sturge, Pub. Van Nostrand). Even with the above mentioned additives, it has not been possible to maintain adequate stability of an infrared sensitive emulsion. As a consequence, many infrared sensitive photographic materials stipulate refrigeration, and put limitations on storage humidity in order to extend the shelf-life as much as possible.

Patents and literature related to supersensitization are listed below.

U.S. Pat. No. 2,875,058 describes the use of triazines such as Leucophor BCF to supersensitize infrared sensitized silver halide emulsions.

U.S. Pat. No. 4,596,767 describes the use of certain heterocyclic salts to supersensitize infrared sensitized silver halide emulsions.

U.S. Pat. No. 4,677,053 shows silver halide emulsions spectrally sensitized to the infrared by quinoline dyes which are supersensitized with diazines or triazines. Dye precursors and polyethylene oxide are also used with the supersensitizer.

U.S. Pat. Nos. 4,030,927 and 4,105,454 describe red and infrared sensitive emulsions which are supersensitized by halogen substituted benzotriazoles and benzotriazole compounds, respectively.

U.S. Pat. No. 3,592,656 describes the supersensitization of merocyanine dye sensitized silver halide emulsions with heterocyclic compounds selected from pyrazoles, 5-pyrazolones, 3-pyrazolones, 3,5-pyrazolidenediones, triazoles, tetrazoles, xanthines, imidazoles, imidazolidines, and imidiazolinium salts.

U.S. Pat. No. 3,457,078 describes the use of mercapto substituted oxazine, oxazole, thiazole, thiadiazole, imidazole or tetrazole as supersensitizers in combination with certain cyanine dyes.

U.S. Pat. No. 3,637,393 describes the use of mercaptotetrazoles in combination with certain hydroquinone compounds to reduce fog and increase speed in photographic emulsions.

U.S. Pat. No. 4,536,473 describes the use of water soluble bromides for increased speed and improved shelf life of infrared photographic materials.

Akhmedzyanov et al., Zhurnel Nauchnio i Prikadnoi Fotografi i Kinematograffi 14 (2), 148–149 (1969) and 12 (6), 462–463 (1967), and Demchuk et al., Zhurnel Prikadnoi Specktrosk., 33 (3), 557 (1980), describe the use of triphenylphosphine as a supersensitizer and stabilizer for infrared sensitive silver halide.

U.S. Pat. No. 4,603,104 describe additive IR supersensitization by combining arylmercaptotetrazoles, triazine stilbenes and poly(ethylacrylate).

U.S. patent application Ser. No. 59,932 and 154,293 describe the use of amine thiatriazoles and quaternary ammonium and phosphonium salts respectively for increased speed and improved shelf life of infrared photographic materials.

By incorporating thio or oxy thiatriazoles into silver halide emulsions or the protective topcoat, improvements have been obtained in photographic speed and in the keeping properties of the materials.

SUMMARY OF THE INVENTION

Silver halide emulsions which have been spectrally sensitized to the red or infrared regions of the electromagnetic spectrum show improved sensitivity and aging characteristics with the addition of thio or oxy thiatriazoles. A further extension of the invention is a combination of thio or oxy thiatriazoles or a combination of the thio or oxy thiatriazoles with other supersensitizing classes.

DETAILED DESCRIPTION OF THE INVENTION

Silver halide crystals have an inherent photosensitivity only in the ultraviolet and blue regions of the electromagnetic spectrum. In order to provide the crystals with sensitivity to other portions of the electromagnetic spectrum, dyes are used. These dyes which extend the range of sensitivity of the silver halide are generally referred to as spectral sensitizing dyes. As noted above, supersensitizers increase the efficiency of these spectral sensitizing dyes.

Traditionally, emulsions which have been spectrally sensitized to the red or infrared regions of the spectrum have been sensitized inefficiently. The relative sensitivities of red or infrared sensitized emulsions tend to be lower than the relative sensitivities of emulsions spectrally sensitized to the visible regions of the spectrum. The need for supersensitizers in the red or infrared is therefore considered to be generally very important.

The addition to red or infrared sensitized silver halide photographic emulsions of compounds of formula (I) or (II):

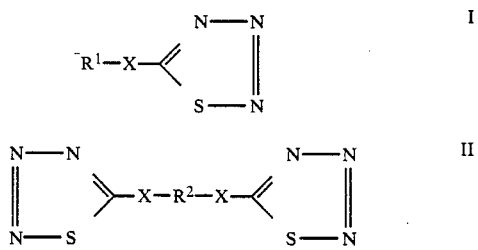

wherein $R^1$ may be a cationic element ($Na^+$, $K^+$, $NH_4^+$, etc.) a proton (H), an acyl (acalkyl), alkyl, aryl, or aralkyl group, or any combination thereof; $R^2$ may be an acyl (acalkyl), alkyl, aryl or aralkyl group; X may be an oxygen or sulfur, or any combination thereof, will increase sensitivity and/or improve the shelf life of the coated materials.

Examples of compounds of the present invention include, but are not limited to, the following:

Formula (I)

T1 5-Thio-1,2,3,4-thiatriazole, sodium salt
T2 5-(4-Chlorobenzoylthio)-1,2,3,4-thiatriazole
T3 5-(4-Cyanobenzoylthio)-1,2,3,4-thiatriazole
T4 5-Phenylacetylthio-1,2,3,4-thiatriazole
T5 5-Napthoylthio-1,2,3,4-thiatriazole
T6 5-Triphenylmethanethio-1,2,3,4-thiatriazole
T7 5-(4-Methylbenzoylthio)-1,2,3,4-thiatriazole
T8 5-Etanoylthio-1,2,3,4-thiatriazole
T9 5-Butanoylthio-1,2,3,4-thiatriazole
T10 5-Hexanoylthio-1,2,3,4-thiatriazole
T11 5-Nonanoylthio-1,2,3,4-thiatriazole
T12 5-Steroylthio-1,2,3,4-thiatriazole
T13 5-Benzylthio-1,2,3,4-thiatriazole
T14 5-Methylthio-1,2,3,4-thiatriazole
T15 5-Ethoxy-1,2,3,4-thiatriazole
T16 5-Phenoxy-1,2,3,4-thiatriazole Formula (II)

T17 5-Glutaroyldi(thio-1,2,3,4-thiatriazole)

These types of compounds are added to the optically sensitized emulsions or to the topcoat in any of the conventional methods by which supersensitizers or other adjuvants are added to photographic emulsions. Typically the supersensitizing compounds of the present invention are added to the emulsion mixture just prior to coating, mixed well, then coated onto the photographic substrate. The compounds are added as aqueous solutions, aqueous dispersions, or organic solvent solutions (e.g., methanol) alone, or with other desirable adjuvants.

The compounds of the present invention may be added in any effective supersensitizing amount to the photographic emulsion or topcoat. The concentration of ingredients and materials can vary significantly in photographic emulsions such as from 0.5 to 10 g/m² for silver. The supersensitizers may also vary significantly in concentration. A generally useful range would be from 0.0001 to 2.0 percent by dry weight of the supersensitizer to the total silver halide emulsion layer. This would generally comprise about 0.001 to 20% by weight of the silver halide in the photographic emulsion layer. A more preferred range would be from 0.01 to 10% for the total supersensitizer combination by weight of the silver halide or about 0.001 to 1.0% total dry weight of the coated emulsion layer.

An extension of the present invention is a combination of the thio or oxy thiatriazoles with an additional compound as described below:
(1) two or more thio or oxy thiatriazoles,
(2) a thio or oxy thiatriazole and an amino thiatriazole,
(3) thio or oxy thiatriazole and an arylmercaptotetrazole, and
(4) a thio or oxy thiatriazole with other supersensitizers.

The arylmercaptotetrazoles useful in the practice of the present invention are defined by the formula

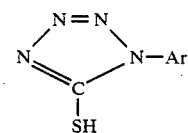

in which Ar is an aryl group, preferably a phenyl group. The aryl or phenyl group may or may not be substituted as with alkyl, alkoxy, pheny, fused benzyl (to form naphthyl groups), halogen (e.g., chloro-, bromo-, fluoro-, and iodo-), amino, sulfonic acid, and carboxyl groups as described in U.S. Pat. No. 3,457,078.

The amino thiatriazoles useful in the practice of the present invention are defined by the formula

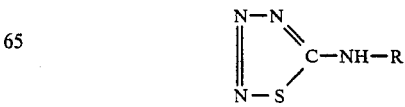

wherein R is selected from the group consisting of alkyl (preferably of 1 to 12 carbon atoms, more preferably of 1 to 4 carbon atoms), aryl (preferably phenyl and substituted phenyl, more preferably p-substituted phenyl, with examples of preferred substituents being selected from the class consisting of halogen (e.g. Br and Cl), hydroxyl, alkyl (e.g. of 1 to 12 carbon atoms, preferably 1 to 4 carbon atoms), alkoxy (e.g. of 1 to 12 carbon atoms, preferably of 1 to 4 carbon atoms), fused aromatic rings (to form naphthyl groups or substituted naphthyl groups with substituents preferred similar to those used with R equals substituted aryl)), allyl, and 5- or 6-membered heterocyclic rings composed of C, S, N, and O atoms, with at least one carbon atom.

Any red or infrared spectral sensitizing dye may be used in the practice of the present invention with the supersensitizing compounds of the present invention. Useful dyes for this purpose tend to be merocyanines, cyanines, dicarbocyanine and especially tricarbocyanines. Such dye sensitizers for the infrared are described for example in U.S. Pat. Nos. 3,457,078, 3,619,154, 3,682,630, 3,690,891, 3,695,888, 4,030,932 and 4,367,800. The preferred classes of compounds are the tricarbocyanines such as the 3,3'-dialkylthiatricarbocyanines, thiatricarbocyanines (especially with rigidized chains), selenotricarbocyanines, and enamine tricarbocyanines. Useful red sensitizing dyes include 4-quinoline, carbocyanine, dicarbocyanine and merocyanine dyes.

Preferred classes of dyes according to the present invention are represented by the following general formula (I), (II) or (III):

d-naphthoselenazole series, [2,1-naphthoselenazole series, thiazoline series, 4-quinoline series, 2-pyridine series, 4-pyridine series, 3,3-dialkyl-indolenine series (wherein alkyl has a meaning known to those skilled in the art including alkyl groups having 1 to 12 carbon atoms), imidazole series and benzimidazole series.

More particularly and preferably, the present invention refers to dyes of the type (I) and (II) above indicated in which both heterocyclic nuclei are of the benzothiazole series. The preferred dyes of the type (III) above in the present invention would be where both heterocyclic nuclei are of the benzoxazole series.

$R^2$ and $R^3$ each represent a hydrogen atom, or an alkyl group having 1 to 5 carbon atoms such as a methyl group or an ethyl group; $R^4$ represents a hydrogen atom, a halogen atom, a hydroxy group, a carboxy group, an alkyl group having 1 to 5 carbon atoms, an unsubstituted or substituted aryl group, or an acyloxy group shown by

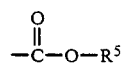

wherein $R^5$ represents an alkyl group having 1 to 5 carbon atoms, a phenyl group, or a substituted phenyl group.

k, l, m, and n are 0 to 1.
Q represents chloride or bromide.
p is 0, 1, 2, or 3.

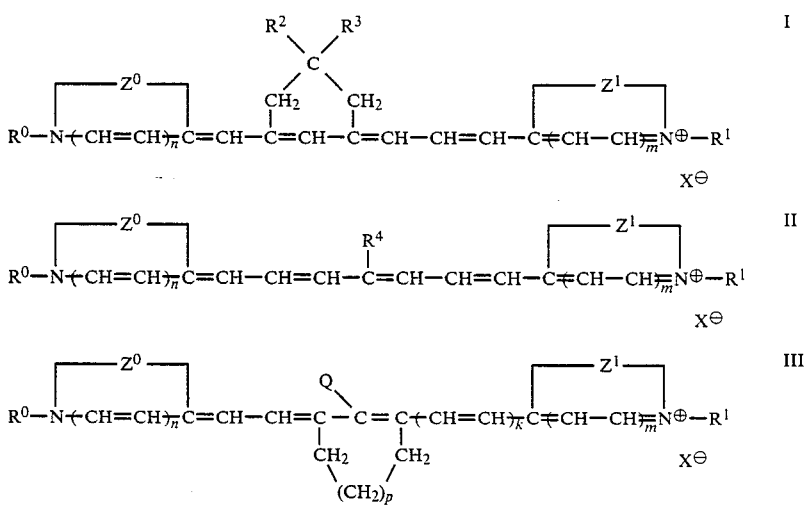

wherein:
$R^0$ and $R^1$ can be a substituted alkyl group or a nonsubstituted alkyl having from 1 to 8 carbon atoms such as, for example, methyl, ethyl, propyl, butyl, amyl, benzyl, octyl, carboxymethyl, carboxyethyl, sulfopropyl, carboxypropyl, carboxybutyl, sulfoethyl, sulfoisopropyl and sulfobutyl groups;
$X^{31}$ is any acid anion such as, for example, chloride, bromide, iodide, perchlorate, sulfamate, thiocyanate, p-toluenesulfonate and benzenesulfonate;
$Z^0$ and $Z^1$ are independently the non-metallic atoms necessary to complete an aromatic heterocyclic nucleus chosen within those of the thiazole series, benzothiazole series, [1,2-d]-naphthothiazole series, [2,1-d]-naphthothiazole series, oxazole series, benzoxazole series, selenazole series, benzoselenazole series, [1,2-

Any of the various types of photographic silver halide emulsions may be used in the practice of the present invention. Silver chloride, silver bromide, silver iodobromide, silver chlorobromide, silver chlorobromoiodide and mixtures thereof may be used for example. Any configuration of grains, cubic orthorhombic, hexagonal, epitaxial, lamellar, tabular or mixtures thereof may be used. These emulsions are prepared by any of the well-known procedures, e.g., single or double jet emulsions as described by Nietz et al., U.S. Pat. No. 2,222,264, Illingsworth, U.S. Pat. No. 3,320,069, McBride, U.S. Pat. No. 3,271,157 and U.S. Pat. Nos. 4,425,425 and 4,425,426.

The silver halide emulsions of this invention can be unwashed or washed to remove soluble salts. In the latter case the soluble salts can be removed by chill-setting and leaching or the emulsion can be coagulation washed e.g., by the procedures described in Hewitson et al., U.S. Pat. No. 2,618,556; Yutzy et al., U.S. Pat. No. 2,614,928; Yackel, U.S. Pat. No. 2,565,418; Hart et al., U.S. Pat. No. 3,241,969; and Waller et al., U.S. Pat. No. 2,489,341.

Photographic emulsions in accordance with this invention can be sensitized with chemical sensitizers, such as with reducing agents; sulfur, selenium or tellurium compounds; gold, platinum or palladium compounds; or combinations of these. Suitable chemical sensitization procedures are described in Shepard, U.S. Pat. No. 1,623,499; Waller, U.S. Pat. No. 2,399,083; McVeigh, U.S. Pat. No. 3,297,447; and Dunn, U.S. Pat. No. 3,297,446.

The silver halide emulsions of this invention can contain speed increasing compounds such as polyalkylene glycols, cationic surface active agents and thioethers or combinations of these as described in Piper, U.S. Pat. No. 2,886,437; Chechak, U.S. Pat. No. 3,046,134; Carroll et al., U.S. Pat. No. 2,944,900; and Goffe, U.S. Pat. No. 3,294,540.

Silver halide emulsions of this invention can be protected against the production of fog and can be stabilized against loss of sensitivity during keeping. Suitable antifoggants and stabilizers which can be used alone or in combination, include the thiazolium salts described in Staud, U.S. Pat. No. 2,131,038 and Allen U.S. Pat. No. 2,694,716; the azaindenes described in Piper, U.S. Pat. No. 2,886,437 and Heimbach, U.S. Pat. No. 2,444,605; the mercury salts described in Allen, U.S. Pat. No. 2,728,663; the urazoles described in Anderson, U.S. Pat. No. 3,287,135; the sulfocatechols described in Kennard, U.S. Pat. No. 3,235,652; the oximes described in Carrol et al., British Pat. No. 623,448; nitron; nitroindazoles; the polyvalent metal salts described in Jones, U.S. Pat. No. 2,839,405; the thiuronium salts described in Herz, U.S. Pat. No. 3,220,839; and the palladium, platinum and gold salts described in Trivelli, U.S. Pat. No. 2,566,263 and Damschroder, U.S. Pat. No. 2,597,915.

Silver halide grains in accordance with the invention can be dispersed in colloids that can be hardened by various organic or inorganic hardeners, alone or in combination, such as the aldehydes, and blocked aldehydes, ketones, carboxylic and carbonic acid derivatives, sulfonate esters, sulfonyl halides and vinyl sulfones, active halogen compounds, epoxy compounds, aziridines, active olefins, isocyanates, carbodiimides, mixed function hardeners and polymeric hardeners such as oxidized polysaccharides, e.g., dialdehyde starch, oxyguargum, etc.

Photographic emulsions according to the present invention can contain various colloids alone or in combination as vehicles or binding agents. Suitable hydrophilic materials include both naturally-occurring substances such as proteins, for example, gelatin, gelatin derivatives (e.g., phthalated gelatin), cellulose derivatives, polysaccharides such as dextran, gum arabic and the like; and synthetic polymeric substances such as water soluble polyvinyl compounds, e.g., poly(vinylpyrrolidone) acrylamide polymers or other synthetic polymeric compounds such as dispersed vinyl compounds in latex form, and particularly those which increase the dimensional stability of the photographic materials. Suitable synthetic polymers include those described, for example, in U.S. Pat. Nos. 3,142,568 of Nottorf; 3,193,386 of White; 3,062,674 of Houck, Smith and Yudelson; 3,220,844 of Houck, Smith and Yudelson; Ream and Fowler, 3,287,289; and Dykstra, U.S. Pat. No. 3,411,911; particularly effective are those water-insoluble polymers of alkyl acrylates and methacrylates, acrylic acid, sulfoalkyl acrylates or methacrylates, those which have cross linking sites which facilitate hardening or curing and those having recurring sulfobetaine units as described in Canadian Pat. No. 774,054.

Emulsions in accordance with this invention can be used in photographic elements which contain antistatic or conducting layers, such as layers that comprises soluble salts, e.g., chlorides, nitrates, etc., evaporated metal layers, ionic polymers such as those described in Minsk, U.S. Pat. Nos. 2,861,056 and 3,206,312 or insoluble inorganic salts such as those described in Trevoy, U.S. Pat. No. 3,428,451.

Photographic emulsions of the invention can be coated on a wide variety of supports. Typical supports include polyester film, subbed polyester film, poly(ethylene terephthalate) film, cellulose nitrate film, cellulose ester film, poly(vinyl acetal) film, polycarbonate film and related or resinous materials, as well as glass, paper, metal and the like. Typically, a flexible support is employed, especially a paper support, which can be partially acetylated or coated with baryta and/or alpha-olefin polymer, particularly a polymer of an alpha-olefin containing 2 to 10 carbon atoms such as polyethylene, polypropylene, ethylenebutene copolymers and the like.

Emulsions of the invention can contain plasticizers and lubricants such as polyalcohols, e.g. glycerin and diols of the type described in Milton, U.S. Pat. No. 2,960,404; fatty acids or esters such as those described in Robijns, U.S. Pat. No. 2,588,765 and Duane, U.S. Pat. No. 3,121,060; and silicone resins such as those described in DuPont British Pat. No. 955,061.

The photographic emulsions as described herein can contain surfactants such as saponin, anionic compounds such as the alkylarylsulfonates described in Baldsiefin, U.S. Pat. No. 2,600,831 fluorinated surfactants, and amphoteric compounds such as those described in Ben-Ezra, U.S. Pat. No. 3,133,816.

Photographic elements containing emulsion layers as described herein can contain matting agents such as starch, titanium dioxide, zince oxide, silica, polymeric beads including beads of the type described in Jelley et al., U.S Pat. No. 2,922,101 and Lynn, U.S. Pat. No. 2,701,245.

Emulsions of the invention can be utilized in photographic elements which contain brightening agents including stilbene, triazine, oxazole and coumarin brightening agents. Water soluble brightening agents can be used such as those described in Albers et al., German Pat. No. 972,067 and McFall et al., U.S. Pat. No. 2,933,390 or dispersions of brighteners can be used such as those described in Jansen, German Pat. No. 1,150,274 and Oetiker et al., U.S. Pat. No. 3,406,070.

Photographic elements containing emulsion layers according to the present invention can be used in photographic elements which contain light absorbing materials and filter dyes such as those described in Sawdey, U.S. Pat. No. 3,253,921; Gaspar, U.S. Pat. No. 2,274,782; Carroll et al., U.S. Pat. No. 2,527,583 and Van Campen, U.S. Pat. No. 2,956,879. If desired, the dyes can be mordanted, for example, as described in Milton and Jones, U.S. Pat. No. 3,282,699.

Contrast enhancing additives such as hydrazines, rhodium, iridium, and combinations thereof are also useful.

Photographic emulsions of this invention can be coated by various coating procedures including dip coating, air knife coating, curtain containing, or extrusion coating using hoppers of the type described in Beguin, U.S. Pat. No. 2,681,294. If desired, two or more layers may be coated simultaneously by the procedures described in Russell, U.S. Pat. No. 2,761,791 and Wynn, British Pat. No. 837,095.

The silver halide photographic elements can be used to form dye images therein through the selective formation of dyes. The photographic elements described above for forming silver images can be used to form dye images by employing developers containing dye image formers, such as color couplers, as illustrated by U.K. Pat. No. 478,984; Yager et al., U.S. Pat. No. 3,113,864; Vittum et al., U.S. Pat. Nos. 3,002,836, 2,271,238 and 2,362,598. Schwan et al., U.S. Pat. No. 2,592,243; Porter et al., U.S. Pat. Nos. 2,343,703, 2,376,380 and 2,369,489; Spath U.K. Pat. No. 886,723 and U.S. Pat. No. 2,899,306; Tuite U.S. Pat. No. 3,152,896 and Mannes et al., U.S. Pat Nos. 2,115,394, 2,252,718 and 2,108,602, and Pilato U.S. Pat. No. 3,547,650. In this form the developer contains a color-developing agent (e.g., a primary aromatic amine which in its oxidized form is capable of reacting with the coupler (coupling) to form the image dye. Also, instant self-developing diffusion transfer film can be used as well as photothermographic color film or paper using silver halide in catalytic proximity to reducable silver sources and leuco dyes.

The couplers may be present either directly bound by a hydrophilic colloid or carried in a high temperature boiling organic solvent which is then dispersed within a hydrophilic colloid. The colloid may be partially hardened or fully hardened by any of the variously known photographic hardeners. Such hardeners are free aldehydes (U.S. Pat. No. 3,232,764), aldehyde releasing compounds (U.S. Pat. No. 2,870,013 and 3,819,608), s-triazines and diazines (U.S. Pat. No. 3,325,287 and 3,992,366), aziridines (U.S. Pat. No. 3,271,175), vinylsulfones (U.S. Pat. No. 3,490,911), carbodiimides, and the like may be used.

The dye-forming couplers can be incorporated in the photographic elements, as illustrated by Schneider et al. *Die Chemie*, Vol. 57, 1944, p. 113, Mannes et al., U.S. Pat. No. 2,304,940, Martinez U.S. Pat. No. 2,269,158, .elley et al., U.S. Pat. No. 2,322,027, Frolich et al., U.S. Pat. No. 2,376,679, Fierke et al., U.S. Pat. No. 2,801,171, Smith U.S. Pat. No. 3,748,141, Tong U.S. Pat. No. 2,772,163, Thirtle et al., U.S. Pat. No. 2,835,579, Sawdey et al., U.S. Pat. No. 2,533,514, Peterson U.S. Pat. No. 2,353,754, Seidel U.S. Pat. No. 3,409,435 and Chen Research Disclosure, Vol. 159, Jul. 1977, Item 15930. The dye-forming couplers can be incorporated in different amounts to achieve differing photographic effects. For example, U.K. Pat. No. 923,045 and Kumai et al., U.S. Pat. No. 3,843,369 teach limiting the concentration of coupler in relation to the silver coverage to less than normally employed amounts in faster and intermediate speed emulsion layers.

The dye-forming couplers are commonly chosen to form subtractive primary (i.e., yellow, magenta and cyan) image dyes and are non-diffusible, colorless couplers, such as two and four equivalent couplers of the open chain ketomethylene, pyrazolone, pyrazolotriazole, pyrazolobenzimidazole, phenol and naphthol type hydrophobically ballasted for incorporation in high-boiling organic (coupler) solvents.

Other conventional photographic addenda such as coating aids, antistatic agents, acutance dyes, antihalation dyes and layers, antifoggants, latent image stabilizers, antikinking agents, and the like may also be present.

Although not essential in the practice of the present invention, one particularly important class of additives which finds particular advantage in the practice of the present invention is high intensity reciprocity failure (HIRF) reducers. Amongst the many types of stabilizers for this purpose are chloropalladites and chloroplatinates (U.S. Pat. No. 2,566,263), iridium and/or rhodium salts, (U.S. Pat. No. 2,566,263; 3,901,713), cyanorhodates (Beck et al., J. Signalaufzeichnungsmaterialen, 1976, 4, 131), and cyanoiridates.

These and other aspects of the invention will be shown by the examples.

SYNTHETIC METHODS

The thio and oxy thiatriazoles were prepared by the synthetic routes outlined in methods A to E.

METHOD A

Preparation of 5-thio-1,2,3,4-thiatriazole, sodium salt

Into a 250 ml Erlenmeyer flask containing 75 ml of deionized water was added 20 grams (0.31 mole) of sodium azide and 25 grams (0.33 mole, slight excess) of carbon disulfide. The flask was stoppered and stirred overnight at room temperature. The yellow solution was filtered and then transferred to a crystallization dish for drying. The resultant solid was dissolved in acetone and filtered. Evaporation of the acetone yielded a yellow-white solid which was characterized by FT-IR and X-ray crystallography.

METHOD B

Preparation of 5 substituted thio-1,2,3,4-thiatriazole

Into a small flask or large test tube was weighed 2.97 grams (0.021 mole) of the sodium salt of 5-thio-1,2,3,4-thiatriazole (see Method A) and 30 ml of acetone to dissolve the solid. Hexanoyl chloride, 2.85 grams (0.021 mole) was added dropwise with vigorous agitation. A yellow white solid precipitate formed almost immediately and was filtered. The solid was rinsed with several small portions of cold water and acetone, then allowed to air dry.

METHOD C

Preparation of 5-methylthio-1,2,3,4-thiatriazole

Potassium hydroxide (33 grams, 0.55 mole) was dissolved in 200 ml of ethanol and slowly added to 85% hydrazine monohydrate (0.55 mole) while stirring in an ice bath. To this solution was added 24 grams (0.52 mole) of carbon disulfide dropwise keeping the temperature between 5° and 10° C. The separation of potassium dithiocarbazinate from the aqueous solution was accomplished by extraction with 2 portions of diethyl ether. Evaporation of the ether gave a clear heavy yellow oil. One half was dissolved in 150 ml of water. After cooling in an ice bath, methyl iodide (39 grams, 0.27 mole) was slowly added in small portions. Agitation continued until the methyl iodide was consumed. The methyl dithiocarbazinate precipitated during this step and was collected and recrystallized from ethanol; m.p.

81°-82° C. The methyl dithiocarbazinate underwent diazotization by sodium nitrite using methods known and published in the literature to yield 5-methylthio-1,2,3,4-thiatriazole; m.p. 34°-35° C.

METHOD D

Preparation of 5phenoxy-1,2,3,4-thiatriazole

Phenyl chlorothionoformate (3.44 grams, 0.02 mole) was dissolved in 5 ml of dry acetone. Sodium azide (1.4 grams, 0.22 mole) was dissolved in 12 ml of deionized water with 8 ml of acetone and slowly added to the phenyl chlorothionoformate solution over a 5 minute period. The reaction was kept at 5° C. in an ice bath and stirred an additional 45 minutes before adding 12 ml of water. The solution was filtered to collect the product; m.p. 35°-36° C.

METHOD E

Preparation of 5-benzylthio-1,2,3,4-thiatriazole

Preparation of the benzyl dithiocarbazinate followed the same procedure as in method C except that benzyl chloride was substituted for methyl iodide. Diazotization to make the target molecule was accomplished by using sodium nitrite by methods reported in the literature.

The preparation of 5-methylthio-1,2,3,4thiatriazole and 5-benzylthio-1,2,3,4-thiatriazole followed standard synthetic procedures reported in the literature for the peparation of thiatriazoles from dithiocarbazinates. These procedures were outlined in methods C and E respectively.

We have found that the addition of methyl iodide or benzyl chloride to the sodium salt of 5-thio-1,2,3,4-thiatriazole yielded two compounds whose infrared spectra (FT-IR) correspond exactly with the FT-IR spectra of the two compounds as prepared in the preceding paragraph by diazotization. Also, their individual melting points were the same and mixed melting points showed on depression. Therefore, the compounds made by different routes were identical.

An x-ray crystal structure was obtained on 5-benxoylthio-1,2,3,4-thiatriazole prepared by method B. This showed the substituted thio form as opposed to the thione (C=S) structure of the molecule.

The preparation methods and melting points are compiled in the table below.

| Thiatriazole | Synthetic Method | m.p. (°C.) |
|---|---|---|
| T2 | B | 96 |
| T3 | B | 94-96 |
| T4 | B | 74-76 |
| T5 | B | 84-86 |
| T7 | B | 91-92 |
| T9 | B | dec* |
| T11 | B | dec* |
| T12 | B | 51-54 |
| T13 | E & B | 68-69 |
| T14 | C & B | 33-35 |
| T15 | C | 40-41 |
| T16 | D | 35-36 |
| T17 | B | dec* |

*Slow decomposition occurred from room temperature upwards.

EXAMPLES

A silver halide emulsion was prepared by a double jet precipitation to provide a grain composed of 64% chloride and 36% bromide with an average size of 0.24 micrometers. The emulsion was digested with p-toluenesulfonica acid, sodium thiosulfate and sodium gold tetrachloride ($NaAuCl_4$).

Final preparation of the emulsion comprised the addition of water and gelatin to the level of 5.0% gelatin and 2500 g of emulsion per mole of silver. The pH was adjusted to 7.0, and the pAg was adjusted to 7.2 Sensitizing dyes (D1-D6), phenyl-5-mercaptotetrazole (hereinafter PMT), p-chloroanilinothiatriazole (hereinafter ClATT) and the thio and oxy thiatriazoles were added as methanol solutions except T1 which was added as an aqueous solution. A 20 gram quantity of poly(ethylacrylate) (hereinafter PEA) was added as a 20% aqueous dispersion to all of the coated films. All additives listed in the tables of the coated films. All additives listed in the tables are given in quantities per mole of silver. The coatings were run at 2.4 g $Ag/m^2$ on 7 mil (0.178 cm) clear polyester base.

The coated and dried films were aged one day before exposing with a flash sensitometer for $10^{-3}$ seconds through either a 660 or 820 nm narrow band filter. The exposed films were developed in a 90 second X-ray processor. Sensitometric results include Dmin, speed (SPD: at O.D =1.0), average contrast (CONT) and the change in log E speed from emulsion without additives (dSPD). Sensitometric evaluation was also run on samples incubated under the extreme conditions of 7 days at 50° C. and 60% R.H., and the speed loss in log E due to incubation (−dSPD) was calculated.

EXAMPLE 1-51

The effects of thio- and oxy-thiatriazoles were evaluated by adding them to the fine grain chlorobromide emulsion sensitized to the near infrared with 30 mg of heptamethine dye, D1. The results are reported in Table 1 for aromatic thio thiatriazoles (T2-T7) and in Table 2 for alkyl thio thiatriazoles (T8-T14) and oxy thiatriazoles (T15 and T16). The dimeric thio thiatriazole, T17, also was included in Table 2 whereas the water soluble sodium salt of thio-thiatriazole (T1) was placed in Table 1. All the sensitometry in Table 1 and 2 was performed with an 820 nm narrow band filter. The thio thiatriazoles of Table 1 show relatively little supersensitization but do show significant benefits when combined with PMT. In all cases, the incubated Dmin in greatly improved by combining any of T1-T7 with PMT. Improvements in incubated speed stability versus the control (Example B) were obtained by adding T1 (Example 4) or T7 (Example 28) to PMT. In these coatings, the fresh speed is lowered but a more stable system results with only a 0.06 log E speed reduction on incubation versus a greater incubated speed loss for the control (example B).

Table 2 shows that the alkyl (T8-T14), dimeric thio thiatriazole (T17) and oxy thiatriazoles (T15 and T16) act as strong supersensitizers with reductions in incubated speed loss at levels exceeding the maximum for fresh speed.

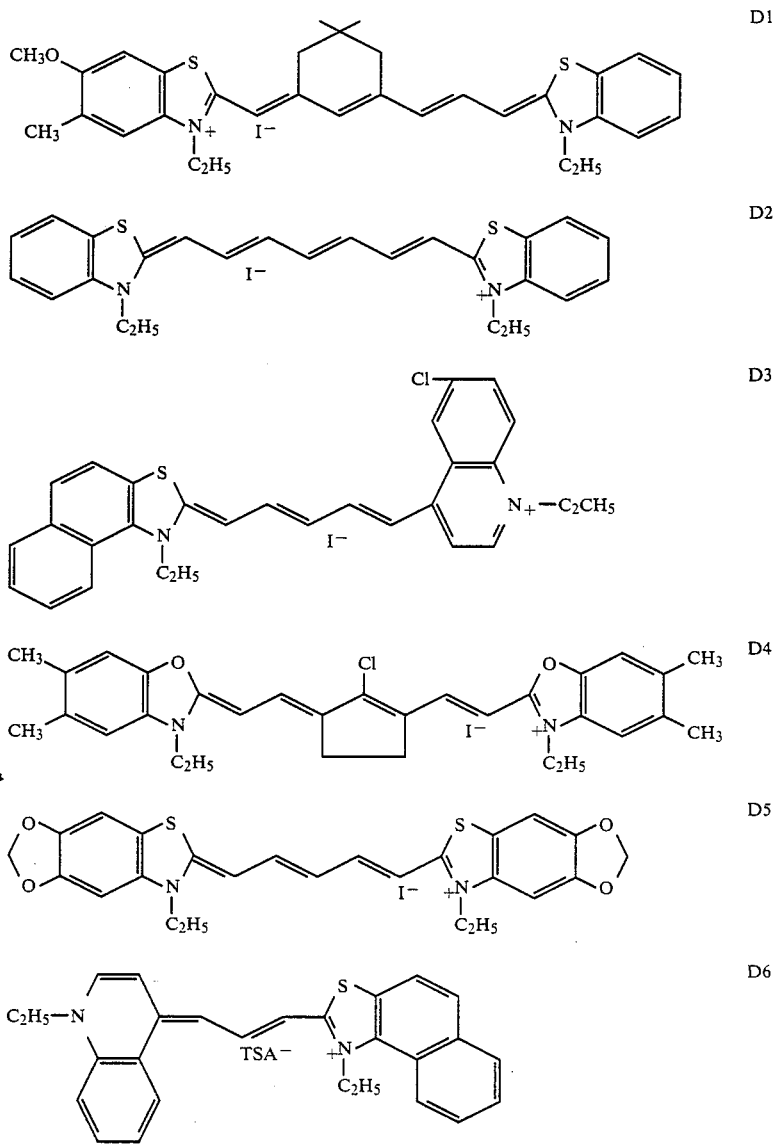
TABLE 1
| Ex. | Thia-triazole (mg/mole) | PMT (mg/mole) | Fresh | | | Incubated 7 Days | | | |
|---|---|---|---|---|---|---|---|---|---|
| | | | Dmin | SPD | CONT | Dmin | SPD | CONT | −dSPD |
| A | — | — | 0.050 | 1.68 | 2.49 | 0.074 | 1.60 | 2.06 | −0.08 |
| B | — | 115 | 0.046 | 2.25 | 2.57 | 0.059 | 2.16 | 2.32 | −0.09 |
| 1 | T1,5 | — | 0.049 | 1.69 | 2.53 | 0.064 | 1.63 | 2.22 | −0.06 |
| 2 | T1,10 | — | 0.049 | 1.67 | 2.52 | 0.058 | 1.61 | 2.18 | −0.06 |
| 3 | T1,5 | 115 | 0.046 | 2.21 | 2.67 | 0.051 | 2.10 | 2.37 | −0.11 |
| 4 | T1,10 | 115 | 0.044 | 2.16 | 2.73 | 0.046 | 2.10 | 2.48 | −0.06 |
| 5 | T2,10 | — | 0.046 | 1.73 | 2.50 | 0.061 | 1.66 | 2.18 | −0.07 |
| 6 | T2,30 | — | 0.045 | 1.73 | 2.53 | 0.053 | 1.68 | 2.29 | −0.05 |
| 7 | T2,10 | 115 | 0.043 | 2.24 | 2.62 | 0.048 | 2.14 | 2.37 | −0.10 |
| 8 | T2,30 | 115 | 0.043 | 2.19 | 2.72 | 0.044 | 2.09 | 2.38 | −0.10 |
| 9 | T3,10 | — | 0.046 | 1.76 | 2.52 | 0.061 | 1.66 | 2.13 | −0.10 |
| 10 | T3,30 | — | 0.044 | 1.77 | 2.49 | 0.051 | 1.66 | 2.15 | −0.11 |
| 11 | T3,10 | 115 | 0.044 | 2.25 | 2.63 | 0.049 | 2.16 | 2.40 | −0.09 |
| 12 | T3,30 | 115 | 0.043 | 2.20 | 2.72 | 0.044 | 2.11 | 2.46 | −0.09 |
| 13 | T4,10 | — | 0.046 | 1.78 | 2.51 | 0.061 | 1.67 | 2.21 | −0.11 |
| 14 | T4,30 | — | 0.046 | 1.78 | 2.54 | 0.054 | 1.70 | 2.27 | −0.08 |
| 15 | T4,10 | 115 | 0.044 | 2.26 | 2.64 | 0.049 | 2.15 | 2.38 | −0.11 |
| 16 | T4,30 | 115 | 0.044 | 2.21 | 2.73 | 0.045 | 2.13 | 2.44 | −0.08 |
| 17 | T5,10 | — | 0.046 | 1.76 | 2.47 | 0.068 | 1.66 | 2.17 | −0.10 |
| 18 | T5,30 | — | 0.046 | 1.73 | 2.53 | 0.066 | 1.67 | 2.19 | −0.06 |
| 19 | T5,10 | 115 | 0.044 | 2.26 | 2.65 | 0.050 | 2.15 | 2.37 | −0.11 |

TABLE 1-continued

| Ex. | Thia-triazole (mg/mole) | PMT (mg/mole) | Fresh Dmin | Fresh SPD | Fresh CONT | Incubated 7 Days Dmin | Incubated 7 Days SPD | Incubated 7 Days CONT | −dSPD |
|---|---|---|---|---|---|---|---|---|---|
| 20 | T5,30 | 115 | 0.043 | 2.22 | 2.74 | 0.046 | 2.13 | 2.38 | −0.09 |
| 21 | T6,10 | — | 0.047 | 1.76 | 2.59 | 0.068 | 1.65 | 2.19 | −0.11 |
| 22 | T6,30 | — | 0.045 | 1.75 | 2.48 | 0.060 | 1.64 | 2.17 | −0.11 |
| 23 | T6,10 | 115 | 0.045 | 2.24 | 2.60 | 0.054 | 2.15 | 2.35 | −0.09 |
| 24 | T6,30 | 115 | 0.044 | 2.23 | 2.65 | 0.049 | 2.13 | 2.38 | −0.10 |
| 25 | T7,10 | — | 0.046 | 1.71 | 2.55 | 0.061 | 1.64 | 2.16 | −0.07 |
| 26 | T7,30 | — | 0.045 | 1.74 | 2.59 | 0.053 | 1.68 | 2.29 | −0.06 |
| 27 | T7,10 | 115 | 0.043 | 2.22 | 2.65 | 0.049 | 2.13 | 2.39 | −0.09 |
| 28 | T7,30 | 115 | 0.042 | 2.15 | 2.67 | 0.045 | 2.10 | 2.51 | −0.05 |

TABLE 2

| Ex. | Thia-triazole (mg/mole) | PMT (mg/mole) | Fresh Dmin | Fresh SPD | Fresh CONT | dSPD | Incubated 7 Days Dmin | Incubated 7 Days SPD | Incubated 7 Days CONT | −dSPD |
|---|---|---|---|---|---|---|---|---|---|---|
| A | — | — | 0.050 | 1.68 | 2.49 | — | | | | |
| B | — | 115 | 0.046 | 2.24 | 2.57 | 0.56 | 0.058 | 2.11 | 2.35 | −0.13 |
| 29 | T8,125 | — | 0.047 | 2.25 | 2.57 | 0.57 | 0.058 | 2.04 | 2.43 | −0.21 |
| 30 | T8,175 | — | 0.048 | 2.32 | 2.61 | 0.64 | 0.056 | 2.14 | 2.43 | −0.18 |
| 31 | T8,250 | — | 0.047 | 2.29 | 2.49 | 0.61 | 0.054 | 2.22 | 2.37 | −0.07 |
| 32 | T9,30 | — | 0.050 | 2.38 | 2.60 | 0.70 | 0.057 | 2.24 | 2.36 | −0.14 |
| 33 | T9,75 | — | 0.055 | 2.37 | 2.57 | 0.69 | 0.059 | 2.30 | 2.31 | −0.07 |
| 34 | T10,175 | — | 0.048 | 2.29 | 2.63 | 0.61 | 0.060 | 2.11 | 2.32 | −0.18 |
| 35 | T10,250 | — | 0.050 | 2.31 | 2.51 | 0.63 | 0.058 | 2.17 | 2.32 | −0.14 |
| 36 | T11,75 | — | 0.049 | 2.31 | 2.59 | 0.63 | 0.057 | 2.16 | 2.40 | −0.15 |
| 37 | T11,125 | — | 0.052 | 2.35 | 2.59 | 0.67 | 0.057 | 2.25 | 2.43 | −0.10 |
| 38 | T11,175 | — | 0.050 | 2.20 | 2.61 | 0.52 | 0.061 | 2.20 | 2.35 | 0 |
| 39 | T12,125 | — | 0.049 | 2.32 | 2.61 | 0.64 | 0.056 | 2.16 | 2.40 | −0.16 |
| 40 | T12,175 | — | 0.050 | 2.35 | 2.59 | 0.67 | 0.056 | 2.21 | 2.35 | −0.14 |
| 41 | T12,250 | — | 0.049 | 2.19 | 2.48 | 0.51 | 0.057 | 2.18 | 2.31 | −0.01 |
| 42 | T17,75 | — | 0.049 | 2.35 | 2.69 | 0.67 | 0.060 | 2.21 | 2.42 | −0.14 |
| 43 | T17,125 | — | 0.050 | 2.25 | 2.39 | 0.57 | 0.062 | 2.23 | 2.25 | −0.02 |
| 44 | T13,150 | — | 0.050 | 1.93 | 2.58 | 0.25 | 0.063 | 1.92 | 2.41 | −0.01 |
| 45 | T13,225 | — | 0.050 | 2.06 | 2.53 | 0.38 | 0.064 | 2.07 | 2.30 | +0.01 |
| 46 | T14,150 | — | 0.048 | 1.86 | 2.44 | 0.18 | 0.063 | 1.70 | 2.36 | −0.16 |
| 47 | T14,225 | — | 0.050 | 1.98 | 2.56 | 0.30 | 0.061 | 1.81 | 2.41 | −0.17 |
| 48 | T15,75 | — | 0.048 | 2.17 | 2.58 | 0.49 | 0.056 | 2.02 | 2.37 | −0.15 |
| 49 | T15,150 | — | 0.049 | 2.29 | 2.49 | 0.61 | 0.053 | 2.18 | 2.45 | −0.11 |
| 50 | T16,150 | — | 0.051 | 2.30 | 2.59 | 0.62 | 0.054 | 2.14 | 2.42 | −0.16 |
| 51 | T16,225 | — | 0.048 | 2.33 | 2.66 | 0.65 | 0.051 | 2.21 | 2.43 | −0.12 |

EXAMPLE 52-57

The additive effects of thio thiatriazoles were tested both with an additional thio thiatriazole and with another strong supersensitizer, p-chloroanilino-1,2,3,4-thiatriazole (ClATT). The chemicals were added to the fine grain chlorobromide emulsion sensitized to the near infrared with 30 mg of heptamethine dye, D1. The sensitometric evaluation was performed with an 820 nm narrow band filter. The results are shown in Table 3. The initial speed was reduced by adding T1 to the two supersensitizers but improvements were found in the incubated data both in terms of lower Dmin and a lower speed drop (−dSPD).

EXAMPLE 58-66

Additional infrared dyes were examined to determine the breadth of the invention. The infrared dyes were added at their optimum level which was 20 mg for D2, 45 mg for D3 and 15 mg/mole Ag for D4. The IR dyes were added to the fine grain chlorobromide emulsion with different levels of 5-nonanoylthio-1,2,3,4-thiatriazole (t11). Sensitometric evaluation was performed with an 820 nm narrow band filter, and the results are listed in Table 4. All three infrared dyes show strong supersensitization in the presence of T11. Therefore, the thiatriazole are not limited as supersensitizers to a specific class of IR dyes, but instead have broad utility as infrared supersensitizers.

TABLE 3

| Ex. | Compound (mg/mole) | Compound (mg/mole) | ClATT (mg/mole) | Fresh Dmin | Fresh SPD | Fresh CONT | Fresh dSPD | Incubated 7 Days Dmin | Incubated 7 Days SPD | Incubated 7 Days CONT | Incubated 7 Days dSPD |
|---|---|---|---|---|---|---|---|---|---|---|---|
| A | — | — | — | 0.049 | 1.67 | 2.44 | — | 0.071 | 1.58 | 2.10 | −0.09 |
| C | — | — | 150 | 0.047 | 2.35 | 2.49 | 0.68 | 0.055 | 2.30 | 2.18 | −0.05 |
| 52 | T1,10 | — | 150 | 0.042 | 2.25 | 2.52 | 0.58 | 0.047 | 2.23 | 2.25 | −0.02 |
| 53 | T1,20 | — | 150 | 0.042 | 2.19 | 2.60 | 0.52 | 0.044 | 2.19 | 2.34 | 0 |
| 54 | T8,120 | — | — | 0.045 | 2.25 | 2.63 | 0.58 | 0.053 | 2.13 | 2.34 | −0.12 |
| 55 | T8,120 | T1,5 | — | 0.045 | 2.21 | 2.65 | 0.54 | 0.051 | 2.11 | 2.39 | −0.10 |
| 56 | T8,120 | T1,10 | — | 0.044 | 2.16 | 2.64 | 0.49 | 0.051 | 2.09 | 2.44 | −0.07 |
| 57 | T8,120 | T1,20 | — | 0.042 | 2.04 | 2.63 | 0.37 | 0.047 | 2.03 | 2.44 | −0.01 |

TABLE 4

| Ex. | Dye | 200 T11 (mg/mole) | Fresh Dmin | SPD | CONT | dSPD |
|---|---|---|---|---|---|---|
| D | D2 | 0 | 0.05 | 1.55 | 2.65 | — |
| 58 | D2 | 75 | 0.04 | 1.86 | 2.78 | 0.31 |
| 59 | D2 | 138 | 0.04 | 2.21 | 2.94 | 0.66 |
| 60 | D2 | 2.72 | 0.04 | 2.28 | 2.89 | 0.73 |
| E | D3 | 0 | 0.07 | 0.85 | 2.72 | — |
| 61 | D3 | 75 | 0.06 | 1.39 | 2.87 | 0.54 |
| 62 | D3 | 138 | 0.06 | 1.66 | 2.66 | 0.81 |
| 63 | D3 | 200 | 0.06 | 1.51 | 2.42 | 0.66 |
| F | D4 | 0 | 0.05 | 1.58 | 2.53 | — |
| 64 | D4 | 75 | 0.04 | 2.12 | 2.81 | 0.54 |
| 65 | D4 | 138 | 0.04 | 2.13 | 2.84 | 0.55 |
| 66 | D4 | 200 | 0.04 | 1.78 | 2.55 | 0.20 |

EXAMPLE 67-69

The thiatriazole, T1, was examined in the protective topcoat layer coated over the emulsion layer. The silver halide emulsion layer was composed of the fine grain chlorobromide emulsion sensitized to the near infrared with 30 mg of heptamethine dye, D1, and supersensitized with 150 mg of ClATT. The emulsion was coated at 2.4 g Ag/m². The thiatriazole, T1, was incorporated into the topcoat layer which was composed of 5% gelatin and coated at 21.5 ml/m². The quantity of T1 is given in Table 5 both in mg of T1 per square meter and in mg of T1 per mole of silver. The sensitometric data in Table 5 was obtained with an 820 nm narrow band filter. The addition of T1 to the adjacent, topcoat layer does drop the fresh speed slightly but improves the fresh and incubated Dmin and reduces the loss of speed on incubation (−dSPD).

TABLE 5

| Ex. | T1 in Topcoat (mg/mole Ag) | T1 in Topcoat (mg/m²) | Fresh Dmin | SPD | CONT | Incubated 7 Days Dmin | SPD | CONT | −dSPD |
|---|---|---|---|---|---|---|---|---|---|
| C | — | — | 0.046 | 2.34 | 2.59 | 0.057 | 2.30 | 2.45 | −0.04 |
| 67 | 3.78 | 0.084 | 0.046 | 2.31 | 2.58 | 0.053 | 2.28 | 2.55 | −0.03 |
| 68 | 7.56 | 0.168 | 0.045 | 2.28 | 2.50 | 0.052 | 2.27 | 2.43 | −0.01 |
| 69 | 15.1 | 0.336 | 0.043 | 2.21 | 2.43 | 0.052 | 2.23 | 2.41 | +0.02 |

EXAMPLE 70-76

The thiatriazoles were examined further in other areas of the electromagnetic spectrum besides the infrared. The red sensitizing dyes, D5 and D6, were both added at 100 mg/mole Ag to the chlorobromide emulsion. The supersensitization effects of the dimeric thiatriazole, T17, were evaluated with a 660 nm narrow band filter and reported in Table 6. The thiatriazole, T17, does improve the speed of red sensitive films and also improved the Dmin on incubation. Therefore, the benefits of the thiatriazoles are not limited to the infrared.

TABLE 6

| Example | Red Dye | T17 (mg/mole) | Fresh Dmin | SPD | CONT | dSPD | Incubated 7 Days Dmin | SPD | CONT | −dSPD |
|---|---|---|---|---|---|---|---|---|---|---|
| G | D5 | 0 | 0.046 | 1.80 | 3.09 | — | 0.058 | 1.74 | 2.73 | −0.06 |
| 70 | D5 | 25 | 0.044 | 1.92 | 3.07 | 0.12 | 0.050 | 1.81 | 2.79 | −0.11 |
| 71 | D5 | 50 | 0.045 | 1.98 | 3.06 | 0.18 | 0.050 | 1.88 | 2.78 | −0.10 |
| 72 | D5 | 75 | 0.048 | 2.03 | 3.12 | 0.23 | 0.049 | 1.93 | 2.79 | −0.10 |
| 73 | D5 | 125 | 0.049 | 2.08 | 3.03 | 0.28 | 0.050 | 1.98 | 2.71 | −0.10 |
| H | D6 | 0 | 0.048 | 1.70 | 2.96 | — | 0.069 | 1.66 | 2.60 | −0.04 |
| 74 | D6 | 25 | 0.047 | 1.76 | 3.02 | 0.06 | 0.058 | 1.69 | 2.67 | −0.07 |
| 75 | D6 | 50 | 0.051 | 1.80 | 2.95 | 0.10 | 0.057 | 1.74 | 2.62 | −0.06 |
| 76 | D6 | 75 | 0.052 | 1.79 | 2.89 | 0.09 | 0.058 | 1.75 | 2.62 | −0.04 |

What is claimed is:

1. A silver halide photographic emulsion in a hydrophilic colloidal binder, said emulsion being spectrally sensitized to the red or infrared portion of the electromagnetic spectrum and having a supersensitizing amount of a 5-substituted-thio- or oxy-1,2,3,4-thiatriazole wherein said 5-substituted-1,2,3,4-thiatriazole is represented by the general formula

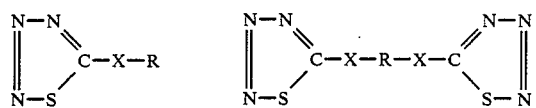

wherein R is selected from the group consisting of alkyl groups, aryl groups, allyl, and 5- or 6-membered heterocyclic groups having only C, N, S or O ring atoms, and X is oxygen or sulfur.

2. The emulsion of claim 1 wherein R is a phenyl group.

3. The emulsion of claim 1 wherein R is an alkyl group.

4. The emulsion of claim 1 wherein R is alkyl.

5. The emulsion of claim 1 wherein poly(ethylacrylate) is also present in a supersensitizing amount.

6. The emulsion of claim 2 wherein poly(ethylacrylate) is also present in a supersensitizing amount.

7. The emulsion of claim 3 wherein poly(ethylacrylate) is also present in a supersensitizing amount.

8. The emulsion of claim 4 wherein poly(ethylacrylate) is also present in a supersensitizing amount.

9. The emulsion of claim 1 wherein two or more thio or oxy thiatriazoles are present.

10. The emulsion of claim 1 wherein an amino-thiatriazole is also present.

11. The emulsion of claim 1 wherein an arylmercaptotetrazole is also present.

12. A photosensitive element comprising a substrate having adhered to at least one surface thereof a layer comprising the photographic emulsion of claim 1.

13. The element of claim 12 wherein said 5-substituted thio- or oxy-1,2,3,4-thiatriazole is present in a protective layer adjacent to said emulsion layer and further from said substrate than said emulsion layer.

14. The emulsion of claim 1 wherein said emulsion is sensitized by a dye selected from the class consisting of thia-, benzothia-, seleno-, benzoseleno-, imida-, benozoimida-, oxa-, benzoxa-, enamine and 4-quinoline carbocyanines, dicarbocyanines, tricarbocyanines and merocyanines.

15. The emulsion of claim 2 wherein said emulsion is sensitized by a dye selected from the class consisting of thia-, benzothia-, seleno-, benzoseleno-, imida-, benozimida-, oxa-, benzoxa-, enamine and 4-quinoline carbocyanines, dicarbocyanines, tricarbocyanines and merocyanines.

16. The emulsion of claim 3 wherein said emulsion is sensitized by a dye selected from the class consisting of thia-, benzothia-, seleno-, benzoseleno-, imida-, benzoimida-, oxa-, benzoxa-, enamine and 4-quinoline carbocyanines, dicarbocyanines, tricarbocyanines and merocyanines.

17. The emulsion of claim 4 wherein said emulsion is sensitized by a dye selected from the class consisting of thia-, benzothia-, seleno-, benzoseleno-, imida-, benzoimida-, oxa-, benzoxa-, enamine and 4-quinoline carbocyanines, dicarbocyanines, tricarboncyanines and merocyanines.

18. The emulsion of claim 1 wherein a supersensitizing amount of an alkyloxy or aryloxy, oxy-1,2,3,4-thiatriazole is present in said emulsion.

19. The emulsion of claim 2 wherein a supersensitizing amount of an oxy-1,2,3,4-thiatriazole is present in said emulsion.

20. The emulsion of claim 3 wherein a supersensitizing amount of an alkyloxy or aryloxy, oxy-1,2,3,4-thiatriazole is present in said emulsion.

21. The emulsion of claim 4 wherein a supersensitizing amount of an oxy-1,2,3,4-thiatriazole is present in said emulsion.

22. The emulsion of claim 12 wherein a supersensitizing amount of an oxy-1,2,3,4-thiatriazole is present in said emulsion.

23. The emulsion of claim 14 wherein a supersensitizing amount of an alkyloxy or aryloxy, oxy-1,2,3,4-thiatriazole is present in said emulsion.

24. The emulsion of claim 1 wherein said emulsion is free of dye-forming couplers.

25. The emulsion of claim 2 wherein said emulsion is free of dye-forming couplers.

26. The emulsion of claim 3 wherein said emulsion is free of dye-forming couplers.

27. The emulsion of claim 4 wherein said emulsion is free of dye-forming couplers.

28. The emulsion of claim 12 wherein said emulsion is free of dye-forming couplers.

* * * * *

UNITED STATES PATENT AND TRADEMARK OFFICE
CERTIFICATE OF CORRECTION

PATENT NO. : 4,914,015
DATED : April 3, 1990
INVENTOR(S) : Philip, Perman and Sills It is certified that error appears in the above-identified patent and that said Letters Patent is hereby corrected as shown below:

Column 4, line 56, "pheny" should be --phenyl--.

Column 8, line 27, "and/or alpha-olefin" should be --and/or an alpha-olefin--.

Column 9, line 20, "Schwan et al., U.S. Pat. No. 2,592,243; Porter" should be --Schwan et al. U.S. Pat. No. 2,950,970; Carroll et al., U.S. Pat. No. 2,592,243; Porter--.

Column 9, line 49, "elley" should be --Jelley--.

Column 11, line 42, "on depression" should be --no depression--.

UNITED STATES PATENT AND TRADEMARK OFFICE
CERTIFICATE OF CORRECTION

PATENT NO. : 4,914,015

DATED : April 3, 1990

INVENTOR(S) : Philip, Perman and Sills

It is certified that error appears in the above-identified patent and that said Letters Patent is hereby corrected as shown below:

Column 13, formula D3

" 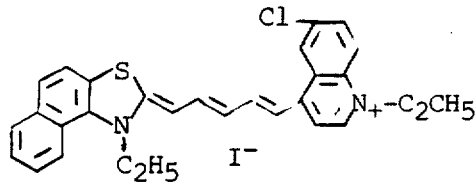 "

should be -- 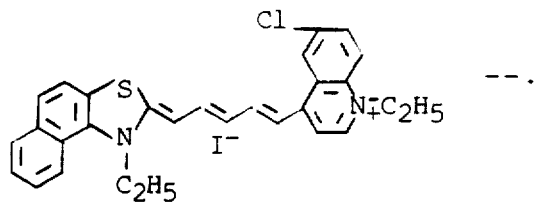 --.

Column 17, lines 2 and 3 (second column in Table 4), "200 Dye" should be --IR Dye--.

Column 17, line 8, "2.72" should be --200--.

Signed and Sealed this

Nineteenth Day of November, 1991

*Attest:*

HARRY F. MANBECK, JR.

*Attesting Officer*     *Commissioner of Patents and Trademarks*